(12) United States Patent  
Allsworth

(10) Patent No.: US 11,298,046 B2  
(45) Date of Patent: *Apr. 12, 2022

(54) BREATH SAMPLING DEVICE AND METHOD

(71) Applicant: OWLSTONE MEDICAL LIMITED, Cambridge (GB)

(72) Inventor: Max Allsworth, Cambridge (GB)

(73) Assignee: OWLSTONE MEDICAL LIMITED, Cambridge (GB)

( * ) Notice: Subject to any disclaimer, the term of this patent is extended or adjusted under 35 U.S.C. 154(b) by 283 days.

This patent is subject to a terminal disclaimer.

(21) Appl. No.: 16/493,366

(22) PCT Filed: Apr. 4, 2018

(86) PCT No.: PCT/EP2018/058608  
§ 371 (c)(1),  
(2) Date: Sep. 12, 2019

(87) PCT Pub. No.: WO2018/185164  
PCT Pub. Date: Oct. 11, 2018

(65) Prior Publication Data  
US 2020/0008710 A1  Jan. 9, 2020

(30) Foreign Application Priority Data  
Apr. 7, 2017 (GB) ..................................... 1705648

(51) Int. Cl.  
*A61B 5/08* (2006.01)  
*A61B 5/097* (2006.01)  
(Continued)

(52) U.S. Cl.  
CPC .............. *A61B 5/097* (2013.01); *A61B 5/082* (2013.01); *A61B 5/6803* (2013.01);  
(Continued)

(58) Field of Classification Search  
CPC ....... A61B 5/097; A61B 5/082; A61B 5/6803; A61B 5/11; A61B 5/6844; G01N 33/497  
See application file for complete search history.

(56) References Cited

U.S. PATENT DOCUMENTS

2004/0131498 A1  7/2004 Kuutti  
2005/0076906 A1 * 4/2005 Johnson .............. A61M 16/024  
128/204.21

(Continued)

FOREIGN PATENT DOCUMENTS

WO          03/000133 A1   1/2003

*Primary Examiner* — Andrey Shostak  
(74) *Attorney, Agent, or Firm* — SZDC Law P.C.

(57) ABSTRACT

Disclosed is apparatus for collecting a breath sample from a human subject, the apparatus comprising at least a mask portion which, in use, is positioned over the subject's mouth and nostrils so as to collect breath exhaled from the subject, the apparatus further comprising movement detection means for detecting movement of the mask portion, and an alarm signal generator, which alarm signal generator generates an alarm signal if the subject's head is outside a predetermined range of acceptable orientations during collection of a breath sample, but only after the subject's head has been outside the predetermined range of acceptable orientations for a defined or measurable period of time.

12 Claims, 2 Drawing Sheets

Figure 1:
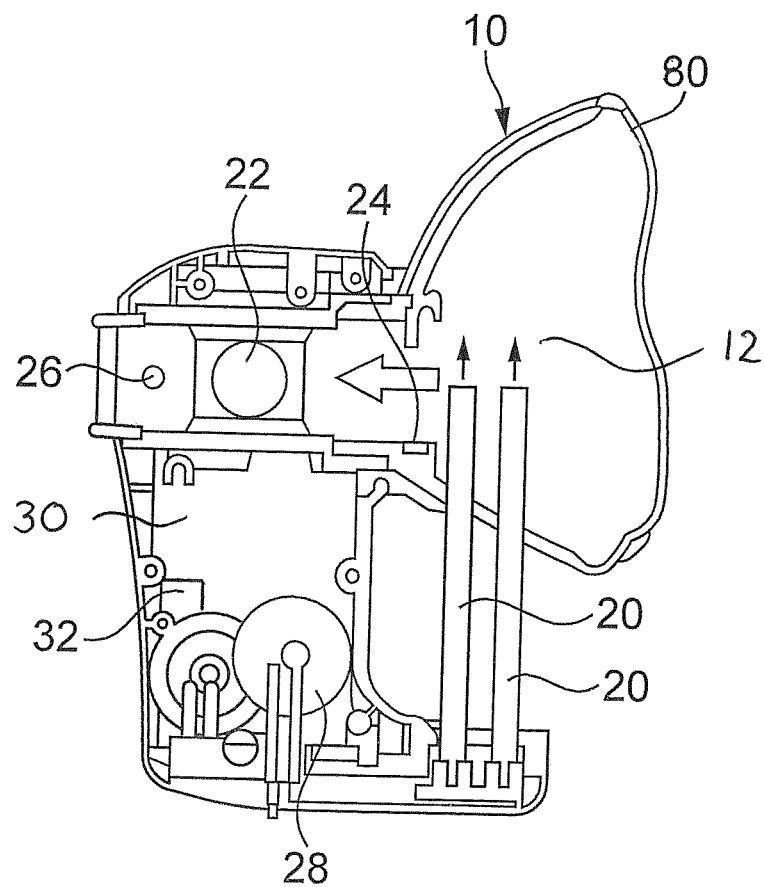

(51) Int. Cl.
  *A61B 5/00* (2006.01)
  *G01N 33/497* (2006.01)
  *A61B 5/11* (2006.01)
(52) U.S. Cl.
  CPC .............. *G01N 33/497* (2013.01); *A61B 5/11* (2013.01); *A61B 5/6844* (2013.01)

(56) References Cited

U.S. PATENT DOCUMENTS

| | | |
|---|---|---|
| 2006/0249160 A1 | 11/2006 | Scarberry et al. |
| 2012/0097158 A1* | 4/2012 | Matalon .............. A61M 16/021 128/202.18 |
| 2015/0335267 A1* | 11/2015 | Cormier ................ A61B 5/082 600/532 |
| 2015/0367092 A1 | 12/2015 | Goff et al. |
| 2016/0045161 A1* | 2/2016 | Alshaer ................ A61B 5/7282 600/538 |
| 2017/0173291 A1* | 6/2017 | Pedro ................ A61M 16/1055 |

* cited by examiner

BREATH SAMPLING DEVICE AND METHOD

This application is the National Stage Application of PCT/EP2018/058608, filed on Apr. 4, 2018, which claims priority to British Patent Application No.: GB 1705648.2, filed on Apr. 7, 2017, which is incorporated by reference for all purposes as if fully set forth herein.

FIELD OF THE INVENTION

The present invention relates to an improved breath sampling device and to a method of obtaining a sample of breath from a subject, using the improved breath sampling device.

BACKGROUND OF THE INVENTION

The metabolome is the aggregate of small molecules that originate from metabolic processes throughout the body. Metabolomic analysis is appealing for biomedical applications as relatively small changes in gene-expression or protein activity can have a profound effect on the concentrations of downstream metabolites. A significant fraction of these metabolites are volatile. These biomarkers are of specific interest in health and disease as they are excreted through breath, urine, faeces and skin providing non-invasive access. Volatile biomarkers (VBs) consist of both volatile organic compounds (VOCs) and Volatile inorganic compounds (VICs). Examples of VBs implicated in health and disease include alkanes, alkenes, acetone, isoprene, NO, CO and aldehydes.

Any change in the function of an organism changes cellular metabolism by definition. Consequently this affects the metabolome and its volatile fraction. The resulting changes in VBs may therefore serve as biomarkers for assessment of a wide range of normal physiological and pathophysiological processes.

In view of the foregoing, there is interest in obtaining samples of breath from a subject for analysis for detection of one or more biomarkers or other analytes. Apparatus for facilitating the capture of a breath sample from a patient is known, and particular examples include those described in U.S. provisional patent application 62/327,200 and PCT/GB2017/050094. Since these are unpublished as of the date of filing of the present application, a copy of the specification of PCT/GB2017/050094 is annexed hereto for reference.

The device disclosed in PCT/GB2017/050094 comprises a mask portion which, in use, is positioned over a subject's mouth and nose, so as to capture breath exhaled from the subject.

The breath sampling apparatus disclosed in PCT/GB2017/050094 is, in many respects, a considerable improvement on previously available breath sampling apparatus. However, the applicant has found a problem associated with the device disclosed in PCT/GB2017/050094.

If, during the period of breath sampling, the subject's head tilts forwards towards the chest, the subject's airways tend to become constricted, which restricts the flow of exhaled air. This may mean that the apparatus does not always sample the required volume of breath during the sampling period. (By way of explanation, the concentration of some biomarkers or other analytes of interest in a subject's breath may be very low, such that an extended period of sampling, perhaps as long as 10 minutes, may be required to obtain a sufficient volume of sampled breath if trying to detect low concentration biomarkers or other analytes).

Further, if the subject's head tilts forwards by a relatively large amount, the applicant has found that the fit of the mask portion to the subject's face may be compromised, allowing ambient air to leak between the mask and the subject's face, which dilutes the breath sample.

The present invention aims to ameliorate or overcome these problems.

SUMMARY OF THE INVENTION

In a first aspect the invention provides apparatus for collecting a breath sample from a human subject, the apparatus comprising at least a mask portion which, in use, is positioned over the subject's mouth and nostrils so as to collect breath exhaled from the subject, the apparatus further comprising movement detection means for detecting movement of the mask portion, and an alarm signal generator, which alarm signal generator generates an alarm signal if the subject's head is outside a predetermined range of acceptable orientations during collection of a breath sample, but only after the subject's head has been outside the predetermined range of acceptable orientations for a defined or measurable period of time.

Preferably the mask portion is shaped and configured so as to form a substantially air-tight seal with the subject's face. To facilitate this, the mask portion preferably is formed of a resiliently deformable material such as rubber or a synthetic plastics material such as a synthetic rubber (e.g. silicone rubber).

With the exception of the movement detection means, the breath sampling apparatus may otherwise be generally as described in PCT/GB2017/050094.

The movement detection means may detect relative movement of the mask portion, or may detect absolute movement of the mask portion, or may detect both relative and absolute movement of the mask portion. More especially, in preferred embodiments the movement detection means at least detects angular displacement of the mask portion in at least one axis, preferably in at least two orthogonal axes, and most preferably in three orthogonal axes. In some embodiments the movement detection means detects only angular displacement, and not any other type of movement (such as translational movement). It will be appreciated that, since the mask portion is normally securely positioned on a subject's face, and should not normally move relative to the subject's face, so that detection of movement by the movement detection means typically indicates movement (i.e. at least angular displacement) of the subject's head.

As an illustration, in some embodiments, the movement detection means may comprise an accelerometer. In other embodiments the movement detection means may comprise a gyroscope, more especially a microelectromechanical system (MEMS) gyroscopic sensor. Many different MEMS gyroscopic sensor devices are available, incorporated on integrated microcircuits which can be mounted on printed circuit boards and the like for attachment to the apparatus of the invention.

The movement detection means is most preferably mounted on, or otherwise physically incorporated within, the mask portion of the breath sampling apparatus. Preferably the movement detection means takes the form of or comprises a gyroscopic sensor chip which is able to determine the position of the mask portion in three dimensions and in real time.

Conveniently the gyroscopic sensor chip is mounted on a printed circuit board which forms an intrinsic part of the mask portion of the sampling apparatus. There are many different gyroscopic sensor chip devices which are commercially available and suitable for use in the apparatus of the invention. Examples of suitable chips are available online from Farnell (http://uk.farnell.com/mems-gyroscopes).

The chip is preferably positioned on a part of the mask portion that is distal to the subject's head, such that, for a given angle of head movement by the subject (especially forward and downward tilting movement of the head) the displacement of the gyroscopic sensor chip is maximised.

If the gyroscopic sensor is positioned on a PCB or the like, it may not be easy, or desirable, to relocate the PCB within the mask portion. In this case, it is desirable that the gyroscopic sensor is at least placed on a part of the PCB which is distal to the subject's head.

A MEMS gyroscopic device is preferable to an accelerometer, since the former can provide information on its orientation in orthogonal X, Y and Z axes without requiring reference to other features and without requiring any calibration, whereas an accelerometer cannot. An accelerometer would preferably therefore need to be calibrated before use with each breath sampling subject to be able to determine position within a preset range of values for X, Y and Z.

The apparatus of the invention includes an alarm signal generator. The alarm, responsive to the alarm signal, may provide a visual alarm or an audible alarm, or may provide both a visual and an audible alarm. Desirably the alarm signal generator is also mounted on a PCB in the mask portion (typically the same PCB on which the movement detection means is preferably mounted), but the alarm per se may be provided on the mask portion or on a remotely situated component of the apparatus, such as a computer monitor, laptop or tablet computer or the like.

The alarm signal generator generates an alarm signal when the information output from the movement detection means indicates that the subject's head has moved to a position which is outside a predetermined range of acceptable positions, which are preferably stored in a digital electronic memory operably associated with the apparatus. Conveniently, for example, the apparatus comprises a preset or predetermined range of values for the subject's head orientation in three dimensions (X, Y, Z values), and these predetermined acceptable value ranges may be stored within the memory of the MEMS gyroscopic sensor device, or on a different memory component mounted on the PCB in the mask portion, or even on a remote memory component (e.g. a computer) operably associated with the mask portion (e.g. communicating therewith via a wired signal connection or wirelessly by Bluetooth™ or other wireless signalling connection).

The alarm signal is generated only if the subject's head stays outside the predetermined range of acceptable orientations for at least a measurable or predetermined time period. This is to stop the alarm from being triggered by momentary movements of the subject's head beyond the range of acceptable orientations. For example, the predetermined time period may be any of 3, 4, 5, 6, 7 or 8 seconds, preferably about 6 seconds. Alternatively the measurable time period may be, for example, the time taken for the subject to complete two breath cycles.

In preferred embodiments the apparatus is programmed with or otherwise provided with an acceptable preset value for each of X, Y and Z, and deviation from any one of the preset values of X, Y and Z by more than a predetermined acceptable margin, for the measurable or predetermined time period, results in generation of the alarm signal.

The predetermined acceptable margin may be the same for each of X, Y and Z for simplicity, or one or more of the orientations may have a different predetermined acceptable margin. In one embodiment, each of X, Y and Z has a predetermined acceptable margin of 20° deviation from the preset value, and deviation by more than this amount in any one of the X, Y and Z orientations will cause alarm signal generation.

An audible alarm may comprise a beeper. A visual alarm may comprise one or more warning LEDs or an indication on an LCD or other electronic display screen. Howsoever the alarm is indicated, it prompts the user to require the subject to return their head to an acceptable orientation, or may prompt the subject to do so directly if they have previously been briefed as to the significance of the alarm. The movement detection means detects the corrective movement of the subject's head and once this has returned the subject's head to an orientation within the predetermined acceptable range of values for orthogonal X, Y and Z axes the alarm signal generation is cancelled and the alarm switched off.

In some embodiments of the invention, in the same way that the alarm signal is generated only after the subject's head has been outside the predetermined range of acceptable positions for a predetermined or measurable period of time, the alarm signal may be turned off only after the subject's head has returned to, and stayed within, the predetermined range of acceptable positions for a predetermined or measurable period of time (e.g. about 6 seconds; or the time taken for the subject to complete two breath cycles).

In addition to detecting movement of the subject's head to sub-optimal positions which may inhibit airflow in the patient's airways, the movement detection means may also optionally be used to identify if and when a subject coughs or sneezes. It is useful to identify such events because they can cause significant changes in pressure within the mask portion of the sampling apparatus. These can affect the readings taken by the apparatus and the operation of the breath sampling in undesirable ways. Accordingly data points in the data stream which correlate with events such as subject sneezes or coughs can be neglected, allowing more reliable and consistent breath sampling.

In a second aspect, the invention provides a method of collecting a breath sample from a subject, the method comprising use of breath sampling apparatus in accordance with the first aspect of the invention. More especially the method comprises attaching a mask portion of the aforementioned apparatus to the face of the subject, and collecting breath exhaled by the subject. Typically the sampling period extends over a plurality of breath cycles of the subject and may last for at least 2 minutes, preferably at least 5 minutes, and often for up to 10 minutes.

Figure 2:
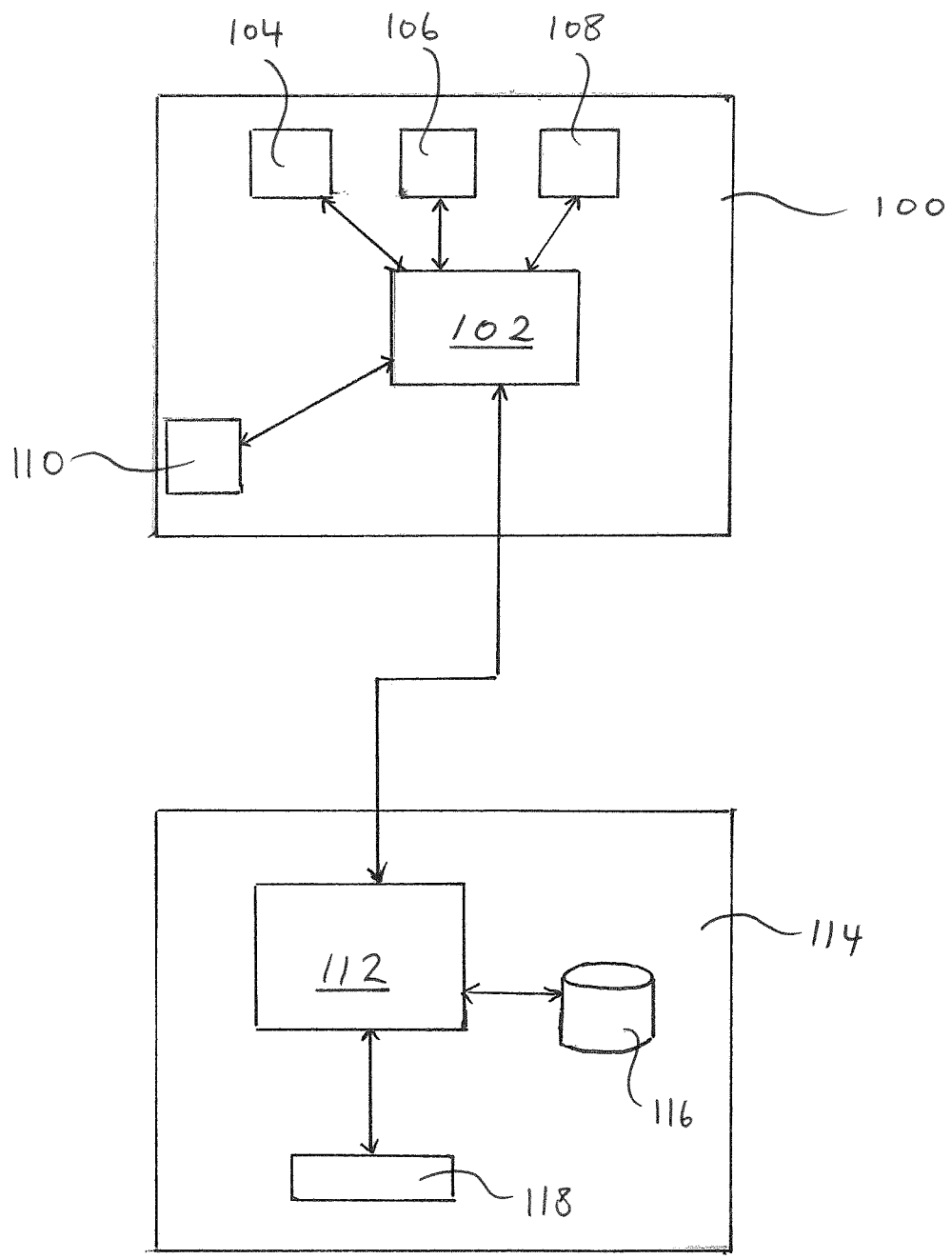

The various features of the invention will now be further described by way of illustrative example and with reference to the accompanying drawings, in which:

FIG. 1 is a sectional view of one embodiment of a mask portion of breath sampling apparatus in accordance with the invention; and FIG. 2 is a schematic diagram showing some of the components of an embodiment of apparatus in accordance with the invention.

DETAILED DESCRIPTION OF AN EMBODIMENT

In one embodiment, breath sampling apparatus in accordance with the first aspect of the invention is generally as described in PCT/GB2017/050094, a copy of which is attached hereto.

Referring to FIG. 1, the breath sampling apparatus comprises a mask portion 10 which is illustrated in cross-section in FIG. 1. In use the mask portion is attached to a subject's face by an elasticated band or the like. The mask portion includes a sealing portion 80 formed of a soft, resiliently deformable, synthetic plastics material (e.g. silicone rubber) which, when pressed to the subject's face, largely forms an air-tight seal with the skin of the subject so as substantially to exclude ambient air from entering the sampling volume 12. The sealing portion 80 covers the subject's mouth and nostrils, such that breath exhaled by the subject enters the sampling volume 12.

The mask portion 10 further comprises:

sorbent tubes (20) for capturing volatile substances contained in the subject's exhaled breath; a $CO_2$ and pressure sensor 22; a replaceable bacterial filter 24; clean air supply 26; pump(s) 28; and a control board 30 for controlling operation of the aforesaid primary components of the mask portion 10.

In particular, mounted on the control board 30 is a MEMS gyroscopic sensor 32, which can determine the orientation of the control board, and hence the mask portion 10 overall, in three dimensions.

The operation of the various components of the mask portion, with the exception of the gyroscopic sensor 32, is generally as described in PCT/GB2017/050094.

The gyroscopic sensor 32 is positioned on control board 30 so as to be distal from the subject's head. In particular the sensor 32 is positioned on or near that part of the control board which is furthest from the subject's head. In this way, movement of the sensor 32 is maximised for a given angular movement of the subject's head.

In use, gyroscopic sensor 32 measurements are recorded once every second, both during an initial 25 second 'training period' and during normal sampling operation of the apparatus. The training period is used to determine suitable trigger points (based on pressure sensor data) used for each pump in order to be able to selectively draw in air (in each breath) from either the subject's upper or lower respiratory tract.

The optimum orientation of the subject's head in terms of orthogonal X/Y/Z axes is preset, either within the MEMS gyroscopic sensor memory, or within memory on a computer.

During operation, when the output of the gyroscopic sensor 32 indicates that the orientation of the subject's head on any of the X, Y or Z axes is outside the optimum preset value (by, e.g., 20 degrees or more), for a period of at least two breath cycles or 6 seconds, then an alarm is triggered. The alarm is generated by the main PCB control board and causes a beeper to sound, and a visual warning to appear on the computer operating the apparatus. The clinician observes this alarm, and prompts the subject to reposition their head. The trigger is released when the gyroscopic sensor detects that the subject's head has returned to within 20 degrees of the preset acceptable orientation along each of the X/Y/Z axes for at least two breath cycles or 6 seconds.

In addition to detecting possibly slow movements which can cause the subject's head to adopt an orientation in which the subject's airways may be constricted, the MEMS gyroscopic sensor 32 can also detect sudden movements of the subject's head (such as may occur during sneezing or coughing), but which might not necessarily cause the subject's head orientation to fall outside of the predetermined acceptable range of values for X, Y and Z. This is useful because the subject sneezing or coughing may cause significant changes in pressure within the mask portion 10, which in turn affect the operation of the pumps 28 (which are triggered using pressure sensor data from pressure sensor 22). Periods in the data stream correlated with events such as sneezes or coughs can be neglected, so that the algorithms can output more suitable triggering points.

EXAMPLE

FIG. 2 is a schematic box diagram showing some of the components of an embodiment of apparatus in accordance with the invention and illustrating their mode of operation.

A printed control board 100 is mounted on the mask portion of "ReCIVA" breath sampling apparatus of the sort described in PCT/GB2017/050094. The control board includes a CPU 102, an $O_2$ sensor 104, a pressure sensor 106 and a valve 108. Also on the control board, and positioned distally, is a MEMS gyroscopic chip 110, which can detect angular displacement of the control board 100 in each of three orthogonal axes, X, Y and Z. Since the gyroscopic chip 110 is positioned distally on the control board, any angular displacement of the subject's head causes maximal displacement of the chip 110. The CPU 102, in response to signals from sensors 104, 106, controls opening and closing of valve 108, which allows selective sampling of the subject's exhaled breath, The CPU 100 on the mask portion is in communication, either by wired link or wirelessly, with the CPU 112 on an external device such as pc, laptop or tablet 114. The CPU 112 is operably connected to a digital electronic memory 116 and an audible and visual alarm 118. Information from the gyroscopic clip 110 indicates if movement of the subject's head causes the mask portion to fall outside a range of predetermined acceptable orientations in the X, Y and Z axes for a period of time in excess of a preset limit. This causes the CPU 102, or the CPU 112, to send an alarm generation signal to the audible/visual alarm 118 on the external device 114. The alarm may be cancelled by a manual input from a user, or by feedback from the gyroscopic chip 110 indicating that the subject's head orientation has returned to within an acceptable range of X, Y and Z values.

The invention claimed is:

1. An apparatus for collecting a breath sample from a human subject, the apparatus comprising at least a mask portion which, in use, is configured to be positioned over the subjects mouth and nostrils so as to collect breath exhaled from the subject, the mask portion comprising sorbent tubes for capturing volatile substances contained in the subject's exhaled breath; the apparatus further comprising a movement detector for detecting movement of the mask portion, and an alarm signal generator, which alarm signal generator generates an alarm signal if the mask portion is outside a predetermined range of acceptable orientations during collection of the breath sample, but only after the mask portion has been outside the predetermined range of acceptable orientations for a defined or measurable period of time.

2. The apparatus according to claim 1, wherein the movement detector detects at least angular displacement of the mask portion.

3. The apparatus according to claim 2, wherein the movement detector detects angular displacement of the mask portion in at least two orthogonal axes.

4. The apparatus according to claim 3, wherein the movement detector detects angular displacement of the mask portion in three orthogonal axes.

5. The apparatus according to claim 1, wherein the movement detector comprises a MEMS device.

6. The apparatus according to claim 1, wherein the movement detector comprises an accelerometer or a gyroscopic sensor device.

7. The apparatus according to claim 1, wherein the movement detector is mounted on a control board housed within the mask portion.

8. The apparatus according to claim 1, comprising a digital electronic memory which stores the predetermined range of acceptable orientations for the mask portion during collection of the breath sample.

9. The apparatus according to claim 8, wherein the predetermined range of acceptable orientations is stored as a range of acceptable values for orthogonal X, Y and Z axes.

10. The apparatus according to claim 1, comprising an audible and/or visual alarm.

11. A method of collecting a breath sample from a subject, the method comprising using a breath sampling apparatus in accordance with claim 1.

12. The method according to claim 11, comprising the steps of attaching the mask portion to the subject's face, and collecting breath exhaled by the subject.

\* \* \* \* \*